United States Patent [19]

Roze

[11] Patent Number: 5,061,732

[45] Date of Patent: Oct. 29, 1991

[54] PORCUPINE-PROOF RESIN FORMULATION AND METHOD

[76] Inventor: Uldis Roze, 240-37 Depew Ave., Douglaston, N.Y. 11363

[21] Appl. No.: 468,192

[22] Filed: Jan. 22, 1990

[51] Int. Cl.$^5$ ...................... A01N 35/02; A01N 35/00
[52] U.S. Cl. ..................................... 514/696; 514/693
[58] Field of Search ................ 424/679, 688; 428/529; 514/693, 694, 731, 696

[56] References Cited

U.S. PATENT DOCUMENTS

| | | | |
|---|---|---|---|
| 3,761,376 | 6/1972 | Okazaki et al. | 204/406 |
| 4,186,242 | 1/1980 | Holmquist | 428/528 |
| 4,244,846 | 1/1981 | Edler | 524/14 |
| 4,524,164 | 6/1985 | Viswanathan et al. | 524/14 |
| 4,758,478 | 7/1988 | Daisy et al. | 428/529 |

FOREIGN PATENT DOCUMENTS 211572  7/1984  German Democratic Rep.

OTHER PUBLICATIONS

Chemical Abstracts (102:114126a) 1985.
Chemical Abstracts (110:115736b) 1989.

*Primary Examiner*—Frederick E. Waddell
*Assistant Examiner*—Kevin Weddington
*Attorney, Agent, or Firm*—Ostrager & Chong

[57] ABSTRACT

Based upon the discovery thata porcupine attack of wood structures is due to the presence of sodium in the conventional resin used in the wood structures, the invention provides for replacing the base used in wood processing with potassium hydroxide or ammonium hydroxide or any other non-sodium base. Potassium hydroxide is found to be a specific deterrent to porcupines. A preferred resin formulation contains potassium hydroxide as the base, and an additive of potassium chloride in an amount of from 5% to 20%, and preferably 10%, by weight of the potassium hydroxide. The potassium-containing resin formulation may be used to make potassium-containing wood products, applied as an adhesive for gluing together wood objects accessible outdoors, mixed with a water-insoluble gum or paint or used to make potassium-containing panelling or shingles which are applied to existing wood structures to render them porcupine-proof.

3 Claims, No Drawings

PORCUPINE-PROOF RESIN FORMULATION AND METHOD

FIELD OF THE INVENTION

This invention generally relates to a composition and method for deterring porcupine attack of wood, and particularly to a porcupine-proof resin formulation which is impregnated in wood.

BACKGROUND ART

Where Indians saw in the porcupine a valuable resource, twentieth century inhabitants of North America have treated the animal as a pest that destroys property and damages timber. Porcupines chew on wood structures, particularly those made of plywood, in wooded, rural areas throughout Canada and Alaska and northeastern, northern, and western regions of the United States. This behavior causes particularly heavy damage to outbuildings such as sheds and barns and vacation houses which are not continuously occupied, as well as to wood implements, canoes, etc.

Until recently, many states offered bounties for porcupines killed, and some undertook massive poisoning programs. Porcupine eradication programs are costly and often proceed blindly without the necessary monitoring for proper biological control. Accordingly, it is desirable to find an inexpensive way to deter porcupines from attacking wood structures which would be easy to administer and present a low risk of irreversible ecological impact.

SUMMARY OF THE INVENTION

It has been discovered through biological and chemical research by the present inventor that the reason that porcupines attack wood buildings and other objects is the presence of sodium in the wood. While most wild herbivores seek out natural sources of sodium, porcupines are unique in exploiting man-made sodium sources wherever they may be available. Objects that contain no sodium, or which contain potassium or a high ratio of potassium to sodium, are not attacked.

In commercial processed plywood, sodium is widely used as part of the glue resin. The phenol-formaldehyde or ureaformaldehyde copolymers commonly used as plywood bonding agents undergo polymerization under basic conditions, and the base typically used in the plywood industry is sodium hydroxide (caustic soda). Thus, the presence of large amounts of sodium residue in the plywood is identified as the target of porcupines. It is also found that vehicles are sometimes disabled by porcupines because the sodium in road salt that becomes encrusted on the underbodies of the vehicles attracts them to chew on tires, hoses, electrical wiring, and other vulnerable parts.

In accordance with the present invention, a method of deterring porcupine attack of a wood product, such as plywood, comprises replacing the base used in plywood processing with potassium hydroxide or ammonium hydroxide or any other non-sodium base. Potassium hydroxide is preferred because it is found that the potassium ion is a specific deterrent to porcupines. Traces of sodium hydroxide may be present in the resin formulation as long as there is a high ratio of 100:1 or more of potassium to sodium. Potassium chloride in an amount of from 5% to 20%, and preferably 10%, by weight of the potassium hydroxide may be added to the resin formulation to render it even more of a deterrent to porcupines.

A further aspect of the invention is a method and formulation for deterring porcupine attack of existing wood structures, particularly those made of sodium-processed plywood, comprising applying a resin gum or paint containing potassium in a water-insoluble form to such wood structures to a height above the ground and down to the ground to mask the sodium-containing wood from the porcupines. A related method is the sheathing of the sodium-containing wood with potassium-containing panels or shingles.

The further features and advantages of the present invention will become more apparent from the following detailed description of the invention.

DETAILED DESCRIPTION OF THE INVENTION

The present inventor has discovered that the porcupines' strong attraction to sodium-containing wood structures and other objects can be deterred by replacing the sodium with potassium, or a high ratio of about 100:1 or more of potassium to sodium, in processed materials, or by masking or sheathing existing sodium-containing structures with potassium-containing resin gum, paint, panelling or shingles.

Phenol-formaldehyde resins are widely used as adhesives and binders in many wood products, including structural wood products such as plywood, particleboard, fiberboard, etc. Plywood is a glued-wood panel that is composed of relatively thin layers or plies of wood veneer with the grain of adjacent layers oriented at an angle to each other. In general, the plies are dried to remove moisture to a level that is compatible with gluing. The plies are coated with a liquid phenol-formaldehyde glue, front and back as appropriate, with a glue applicator. Heat and pressure are applied in a hot press to cure the glue and bond the plies together to form the plywood.

In commercially processed plywood, the conventional liquid glue resins used in the plywood employ a sodium hydroxide (caustic soda) base. The resin solution requires an alkalinity content, and typically contains in the range of 1% to about 15%, and preferably 2% to 8%, by weight of sodium hydroxide. In accordance with the invention, the sodium hydroxide of conventional liquid glue resins used in plywood processing is replaced with potassium hydroxide or ammonium hydroxide or any other base which would create the basic condition for the resin. Potassium hydroxide is preferred because the potassium ion is found to be a specific deterrent to porcupines. The base may contain a mixture of potassium with small or trace amounts of sodium, as long as the ratio of potassium to sodium is kept high. It is found that a ratio of 100:1 or more maintains the deterrent effect on porcupines. In addition, it is found that the addition of from 5% to 20%, and preferably in the range of 10%, by weight of potassium chloride to potassium hydroxide increases the deterrent effect. The amount of potassium chloride additive is limited in order not to increase water solubility to too great an extent.

It is found in tests that potassium-containing plywood processed as described above is not attacked by porcupines. In addition to use in outbuildings, such potassium-containing plywood can be used in the construction of objects, such as canoes, shelters, fencing, etc. which are accessible to porcupines outdoors, in order to render them unattractive to the porcupines.

As a further aspect of the invention, the potassium-containing resin can be mixed together with a water-insoluble gum or paint which can be applied or painted on existing sodium-containing wood structures to deter porcupine attack. The potassium-containing resin is modified to a water-stable form to render the protective formulation impervious to wet or humid outdoor conditions.

In addition, existing sodium-containing wood structures can be sheathed in potassium-containing plywood panelling or shingles in order to mask the sodium with the potassium deterrent. For example, thin plywood panels, e.g. ¼ inch plywood, containing the potassium resin can be cut in panels of 2- or 4-foot widths and 2-foot heights and installed as a protective skirt around the base of an existing wood structure. Similarly, potassium-containing shingles may be used.

Although the invention has been described with reference to certain preferred methods and embodiments, it will be appreciated that many variations and modifications may be made consistent with the broad principles of the invention. It is intended that the preferred embodiments and all of such variations and modifications be included within the scope and spirit of the invention, as defined in the following claims.

I claim:

1. A method of deterring a porcupine attack of a wood structure comprising the step of applying a mask to the wood structure, said mask containing a liquid phenol-formaldehyde resin employing an alkaline base selected from the group of potassium hydroxide, ammonium hydroxide, and other non-sodium base.

2. A method according to claim 1, wherein said non-sodium base is potassium hydroxide in an amount of from 1% to 15% by weight of the resin formulation.

3. A method according to claim 1, wherein the non-sodium base contains a mixture of potassium hydroxide with sodium hydroxide in a ratio of of 100:1 or more.

* * * * *